US006596016B1

(12) United States Patent
Vreman et al.

(10) Patent No.: US 6,596,016 B1
(45) Date of Patent: Jul. 22, 2003

(54) PHOTOTHERAPY OF JAUNDICED NEWBORNS USING GARMENTS CONTAINING SEMICONDUCTOR LIGHT-EMITTING DEVICES

(75) Inventors: Hendrik J. Vreman, Los Altos, CA (US); Daniel S. Seidman, Tel-Aviv (IL); David K. Stevenson, Los Altos Hills, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 0 days.

(21) Appl. No.: 09/551,946

(22) Filed: Apr. 19, 2000

Related U.S. Application Data

(63) Continuation-in-part of application No. 09/094,231, filed on Jun. 9, 1998, now Pat. No. 6,350,275, which is a continuation-in-part of application No. 08/824,631, filed on Mar. 27, 1997, now abandoned.
(60) Provisional application No. 60/049,230, filed on Jun. 9, 1997.

(51) Int. Cl.[7] .................................................. A61N 5/06

(52) U.S. Cl. ............................. 607/88; 607/91; 2/906; 600/310; 600/315; 128/903; 128/904

(58) Field of Search ......................... 607/88, 91; 2/905, 2/906; 128/903, 904; 600/310, 315

(56) References Cited

U.S. PATENT DOCUMENTS 3,877,437 A 4/1975 Maitan et al.
4,441,049 A 4/1984 Verstegen et al.
4,480,293 A 10/1984 Wells (List continued on next page.)

OTHER PUBLICATIONS

Goethe, *Why use homeopathic doses of phototherapy?*, Pediatrics, 98(2), pp. 283–287, 1996.
Kang, J. et al., *Double phototherapy with high irradiance compared with single phototherapy in neonates with hyperbilirubinemia*, Am. Jour. Perinatology, 12(3), pp. 178–179, 1995.
George, P et al., *Ohmeda biliblanket vs wallaby phototherapy system for the reduction of levels in the home care setting*, Clinical Pediatrics, pp. 178–180, 1994.

Primary Examiner—David M. Shay
(74) Attorney, Agent, or Firm—Lumen Intellectual Property Services, Inc.

(57) ABSTRACT

A phototherapy garment contains a flexible backing material, a transparent liner, and a flexible printed circuit sheet containing surface-mounted light-emitting diodes (LEDs) positioned between the backing material and the liner. An infant is placed inside the garment so that the LEDs illuminate a large portion of the infant's skin for phototherapy. The LEDs preferably emit high-intensity blue light, suitable for treatment of neonatal hyperbilirubinemia or Crigler-Najjar syndrome. The LEDs are arranged in a densely packed array facing the liner and emit uniform, high intensity light. A power supply, which may be portable, supplies adjustable power to the LEDs, preferably pulsed with a duty cycle of approximately 10%, and preferably to overdrive the LEDs to maximize light output. A two-way communications device incorporated into the garment allows a physician or computer to control the garment remotely and gather relevant information periodically or continuously. The garment may also contain a feedback system with skin bilirubin sensors, so that the intensity level and duration of light therapy can be based on bilirubin in the skin, which is a reflection of the newborn's serum bilirubin concentration. The garment can be of any type, including sacs, hats, sweaters, jackets, and rompers, and is lightweight and portable, allowing an infant to be treated at home, in the hospital, or when in transit. The garment provides high light intensity over a larger surface area of the newborn than allowed with existing techniques, thus providing very efficient phototherapy.

38 Claims, 5 Drawing Sheets

U.S. PATENT DOCUMENTS

| | | |
|---|---|---|
| 5,005,108 A | 4/1991 | Pristash et al. |
| 5,045,983 A | 9/1991 | Shields |
| 5,278,432 A | 1/1994 | Ignatius et al. |
| 5,339,223 A | 8/1994 | Kremenchugsky et al. |
| 5,358,503 A | 10/1994 | Bertwell et al. |
| 5,698,866 A | 12/1997 | Doiron et al. |
| 6,045,575 A * | 4/2000 | Rosen et al. ................ 2/905 |
| 6,145,551 A * | 11/2000 | Jayaraman et al. ........... 2/905 |

* cited by examiner

PHOTOTHERAPY OF JAUNDICED NEWBORNS USING GARMENTS CONTAINING SEMICONDUCTOR LIGHT-EMITTING DEVICES

CROSS-REFERENCE TO RELATED APPLICATIONS

This application is a continuation-in-part of application Ser. No. 08/824,631, filed Mar. 27, 1997 now abandoned, which is herein incorporated by reference. This application is also a continuation-in-part of application Ser. No. 09/094,231, filed Jun. 9, 1998 now U.S. Pat. No. 6,350,275, which claims the benefit of U.S. Provisional Application No. 60/049,230 filed Jun. 9, 1997, both of which are herein incorporated by reference.

FIELD OF THE INVENTION

This invention relates generally to treatment of neonatal hyperbilirubinemia (jaundice). More particularly, it relates to phototherapy methods and devices containing light-emitting diodes.

BACKGROUND ART

Approximately 60% of the four million infants born in the United States each year become clinically jaundiced. Jaundice, or hyperbilirubinemia, results from increased production and transiently impaired elimination of the pigment bilirubin. While most affected neonates recover rapidly, some infants show persistent high levels of unconjugated bilirubin. Such high levels can lead to kernicterus, a condition involving deposition of bilirubin in the brain, which leads to deficits in cognition, neuromuscular tone and control, and hearing, and even death. The most common therapy for neonatal hyperbilirubinemia is phototherapy. It is estimated that as many as 400,000 neonates in the United States receive phototherapy every year.

Phototherapy facilitates the transformation of unconjugated bilirubin to compounds that are more easily excreted. Bilirubin undergoes in parallel three reactions: photooxidation, configurational isomerization, and structural isomerization. Structural isomerization is the predominant mechanism leading to bilirubin elimination from the bloodstream. Structural isomerization transforms bilirubin instantaneously and continuously into the more polar non-toxic pigment lumirubin, which is presumably the major bilirubin product excreted in newborns undergoing phototherapy. The wavelength range generally effective for facilitating bilirubin photoisomerization is approximately 400–550 nm (violet to green), with light of a wavelength between 450 and 460 nm (blue) yielding maximal photoisomerization. For general information on hyperbilirubinemia and phototherapy, see for example the articles by the Provisional Committee for Quality Improvement and Subcommittee on Hyperbilirubinemia (American Academy of Pediatrics) in *Pediatrics* 94:558–565 (1994), Ennever in *Clin. Perinatol.* 17:467–481 (1990), and Maisels in *Neonatology: Pathophysiology and Management of the Newborn*, 4th Edition, J. B. Lippincott Co., Philadelphia, p. 630–735, as well as the books by Volpe, *Neurology of the Newborn*, W. B. Saunders Co., Philadelphia, 1995, and Brown and McDonagh, *Phototherapy for Neonatal Hyperbilirubinemia: Efficacy, Mechanism, and Toxicity*, Year-Book Medical Publishers, 1980.

The efficacy of phototherapy depends on four main factors: irradiance (light intensity), spectral range (wavelength or color), exposed skin surface area, and duration of exposure. Irradiance is a measurement of the light energy incident on the skin, in units of $\mu W/cm^2/nm$ (power per surface area per wavelength). For a given light source power, the irradiance can be increased by decreasing the distance between the light source and the newborn. Lumirubin formation is not only wavelength-dependent, but is also stimulated by higher light intensities, as discussed in the article by G. Agati et al. in *J. Photochem. Photobiol., B: Biol.* 17:173–180 (1993). Proper evaluation of phototherapy devices and techniques requires assessment of each of these four factors, as well as consideration of potential side effects.

Phototherapy for treating hyperbilirubinemia is commonly delivered using fluorescent lamps suspended above the neonate. However, these conventional phototherapy devices have substantial drawbacks. While fluorescent lamps output high-intensity light, they also generate significant heat (infrared radiation), which prevents their placement close to the infant, thereby decreasing the irradiance. Fluorescent light is of a broad spectral range, and cannot be produced in only the narrow wavelength range desired. Conventional phototherapy devices typically illuminate the newborn only from above, and do not therefore make optimal use of the available skin area. U.S. Pat. No. 3,877,437 to Maitan et al. describes an apparatus for simultaneous bilateral phototherapy of neonates, from both above and below, thus effectively doubling the exposed surface area of the infant. The apparatus uses fluorescent lamps and thus subjects the neonate to side effects discussed below.

The use of fluorescent lamps for phototherapy leads to adverse side effects in many newborns. Such side effects include increased insensible water loss, hypothermia, loose and frequent bowel movements, tanning, and potential nasal obstruction by the eye pads required for preventing retinal damage. Furthermore, there are concerns that phototherapy using fluorescent lamps has potentially harmful effects on biological rhythms, and may increase the incidence of skin cancer in neonates subject to repeated treatment. For information on potential side effects of conventional phototherapy treatment see the articles by Wu and Moosa in *Pediatrics* 61:193–198 (1978), Oh and Karecki in *Am. J. Dis. Child* 124:230–232 (1972), Bell et al. in *J. Pediatr.* 94:810–813 (1979), Woody and Brodkey in *J. Pediatr.* 82:1042–1043 (1973), Messner in *Ped. Res.* (Abstr.) 12:530 (1978), Kemper et al. in *Pediatrics* 84:773–778 (1989), and Garden et al. in *Arch. Dermatol.* 121:1415–1420 (1985). In addition, overhead illumination with AC-powered blue light leads to discomfort and vertigo in nursery staff, as explained for example in the article by Wanamaker et al. in *Lighting, Research, and Technology* 7:19 (1975).

Further drawbacks are introduced by the practical design of fluorescent lamps used for phototherapy. The bulky overhead lamps prevent unimpeded access to the baby and interfere with maternal-infant bonding. There is abundant literature regarding possible long-term harm stemming from disturbed maternal-infant bonding. For example, see *Monogr. Soc. Res Child Dev.* 64(3):67–96 (1999) and discussion on pages 213–220; and *J. Child Psychol. Psychiatry* 40(6):929–939 (1999). In the past, newborns typically remained in the hospital for at least three days, and hyperbilirubinemia was treated aggressively during this time. Now, however, most newborns are discharged within 24 or 36 hours, and bilirubin concentrations reach much higher levels before the problem is noticed. Such infants must be readmitted to the hospital for conventional phototherapy treatment, because phototherapy devices are not suitable for home use. Changing conditions demand phototherapy devices that are less expensive and more flexible to use, and particularly those that can be used at home by parents.

Several manufacturers have recently introduced fiberoptic phototherapy systems. Such manufacturers include Ohmeda (Columbia, Md.) and Fiberoptic Medical Products, Inc. (Allentown, Pa.). Typically, light from an incandescent ~150 W tungsten-halogen bulb is delivered to a fiberoptic pad containing interwoven optical fibers having multiple scattering centers. The ends of all of the fibers are bundled together to form a cable into which the light source is directed. When the cable becomes too large in diameter, it is no longer convenient or feasible to use; thus the total optical power delivered to the pad is limited by the cable size. While the fiberoptic pads can be placed adjacent to the neonate (e.g. directly around the infant), the pad sizes and light intensities available with such systems are limited. For a given light source, enlarging the pad requires distributing the light over a greater area, thus reducing the irradiance. To achieve high levels of irradiance, manufacturers must compromise the surface area by reducing the size of the pad, thereby exposing a relatively small surface area of the newborn to the light. Descriptions of fiberoptic phototherapy systems are provided in U.S. Pat. No. 4,234,907 to Daniel and U.S. Pat. No. 5,339,223 to Kremenchugsky et al. For a comparative analysis of two commonly used fiberoptic phototherapy devices, see the article by George and Lynch in *Clinical Pediatrics*, Mar. 1994: 178–180. The authors note the desirability of higher light intensities, and conclude that "in the past, perhaps too much attention has been paid to color and not enough attention has been paid to intensity." Furthermore, Ennever et al. in *J. Pediatr.* 109:119–122 (1986) suggest that "if a method for conveniently delivering phototherapy of much higher intensity were developed without attendant problems associated with high intensity, tungsten filament sources, it could provide substantial improvement in the efficacy of phototherapy."

For further information and analysis of prior art light sources, see the articles by Pratesi et al. in *Photodermatology* 6:244–257 (1989), Donzelli and Pratesi in *SPIE Proceedings of Biomedical Optoelectronic Devices and Systems* 2084:332–344 (1994), and Donzelli et al. in *The Lancet* 346:184–185 (1995).

Recently, devices have been developed that attempt to overcome the problems of low intensity and minimal surface area coverage of prior art phototherapy systems. A thin panel illuminator is disclosed in U.S. Pat. No. 5,005,108 to Pristash et al. Light is input to a transparent panel, conducted through the panel, and then emitted from one of its surfaces. The panel is flexible and may be shaped around a body part for optimum delivery of light to the required areas. However, this panel suffers from the same intensity problem as fiberoptic panels. The light is generated in a location that is a distance away from the location of its delivery to the skin, and the resulting power delivered is lower than desirable for phototherapy applications.

U.S. Pat. No. 5,698,866 to Doiron et al. discloses a uniform illuminator for local phototherapy using light-emitting diodes (LEDs) as a light source. LEDs provide significant advantages over fluorescent lamps or fiberoptic systems: narrow spectrum, high intensity at desired wavelengths, small size, relatively low cost, and ability to generate light in direct contact with the skin surface. The illuminator of Doiron includes a handpiece containing an LED array that is connected to a power source. The LEDs are fixed in a particular plane defined by the handpiece. While the device does provide a high irradiance, it covers only a very small region of the skin, and therefore cannot provide the surface area exposure required for treating hyperbilirubinemia using total body phototherapy.

A flexible pad containing diodes used for photo-thermal therapy is disclosed in U.S. Pat. No. 5,358,503 to Bertwell et al. Over a given skin region, the pad's flexibility allows all of the diodes to be positioned with their longitudinal axes perpendicular to the skin. However, the device is not suitable for covering a large surface area of a neonate, which requires it to conform to the infant's skin and therefore make sharp folds. The lens-type diodes used are also not suitable for supporting the neonate's weight. Finally, the pad is intended to provide both heat and light, and provides no means for cooling the diodes or infant.

There is still a need, therefore, for a phototherapy device that provides high irradiance to a large surface area of the neonate, is inexpensive, consumes relatively low power, can be used outside of a hospital, minimizes discomfort to the neonate and caregivers, operates at the desired wavelength range, and is completely safe for the neonate.

OBJECTS AND ADVANTAGES

Accordingly, it is a primary object of the present invention to provide a phototherapy garment that provides high irradiance to a maximum surface area of a neonate, thereby providing for rapid reduction in serum bilirubin levels.

It is an additional object of the invention to provide a phototherapy device in which light is generated directly adjacent to the neonate's skin without overheating the neonate.

It is another object of the invention to provide a phototherapy garment that is lightweight and portable, allowing the neonate to be treated at home or while in transit.

It is a further object of the invention to provide a phototherapy garment that prevents light from reaching the neonate's eyes, thereby eliminating the need for an eye shield and preventing nausea in nursery staff.

It is another object of the present invention to provide a phototherapy device that provides light that is completely safe to the neonate and causes few if any detrimental side effects.

It is an additional object of the invention to provide a phototherapy garment that is relatively inexpensive and consumes little power.

It is another object of the present invention to provide a phototherapy garment that fully covers the neonate, thereby preventing discomfort and hypothermia.

It is a further object of the invention to provide a phototherapy garment that does not inhibit maternal-infant contact and bonding.

It is an additional object of the invention to provide a phototherapy garment incorporating skin sensors that provide feedback to control activation of the light-emitting diodes.

Finally, it is an object of the invention to provide a phototherapy garment that communicates with a monitoring system using a two-way communications device, allowing remote control and recording of the garment's operating parameters.

SUMMARY

These objects and advantages are attained by a phototherapy garment for treating neonatal hyperbilirubinemia, Crigler-Najjar syndrome, and the like. The garment contains a flexible backing material, a liner sealed to the inside surface of the backing material, and a printed circuit sheet, preferably flexible, secured inside a pocket between the backing material and the liner. The printed circuit sheet contains a printed circuit and a plurality of surface-mounted light-emitting diodes (LEDs) facing the liner, preferably arranged in a densely packed array and generating light that is uniform across the surface of the garment. For example, there may be approximately 16 LEDs per square inch. The array has a longitudinal direction and a transverse direction, and the garment is preferably flexible in the longitudinal direction and the transverse direction. Preferably, the printed circuit sheet covers a majority of the inside surface of the backing material. The LEDs emit light of a wavelength suitable for treating hyperbilirubinemia in neonates, such as 420–500 nm, preferably between 440 and 470 nm. Portions of the backing material, liner, and flexible sheet may be removed to facilitate heat removal through the removed portions, and a heat sink material may also be provided.

The garment may also include a power supply, preferably portable, in electrical communication with the printed circuit for supplying power to the LEDs. The power supply may include means for supplying power intermittently and means for overdriving the LEDs. Preferably, the LEDs are supplied with enough power to generate an irradiance of greater than 30 $\mu W/cm^2/nm$, and most preferably greater than 100 $\mu W/cm^2/nm$. The garment may also contain a communications device, preferably wireless and two-way, for controlling and recording the parameters of LED operation. It may also contain sensors for measuring skin reflectance, as an index for the serum bilirubin concentrations, or properties such as skin temperature, oxygen saturation, glucose blood level, and perspiration.

Adjacent portions of the edge of the backing material may be joined together to define an interior space surrounded by the liner and in which a neonate is placed. Various garments, such as hats, sweaters, jackets, rompers, and sacs, may be formed. In these embodiments, the outer layer of the garment is a flexible shell with the desired shape, and a liner is sealed to the inside surface of the shell, with the printed circuit sheet positioned in between.

The present invention also provides a method of treating a neonate for hyperbilirubinemia including the steps of: providing a garment with a plurality of surface-mounted LEDs that emit light at a wavelength suitable for treating hyperbilirubinemia; covering a skin region of the neonate with the garment so that the LEDs face the skin region; and providing sufficient power to the LEDs to activate them. Preferably, the garment covers a majority of the circumference of the skin region that is being exposed to the light. Power is preferably provided to the LEDs intermittently, with a predetermined frequency and a predetermined duty cycle, which is preferably less than 50%, and most preferably approximately 10%. The method may also include measuring the bilirubin level in the skin, which is related to the pigment's concentration in circulating blood of the neonate. The jaundice level of the skin is used to control activation, intensity, and duty cycle of the LEDs. The method may also include controlling LED activation remotely. The method can also be used to treat a patient with Crigler-Najjar syndrome.

DETAILED DESCRIPTION

Although the following detailed description contains many specifics for the purposes of illustration, anyone of ordinary skill in the art will appreciate that many variations and alterations to the following details are within the scope of the invention. Accordingly, the following embodiments of the invention are set forth without any loss of generality to, and without imposing limitations upon, the claimed invention.

The present invention provides a phototherapy garment used for treating neonatal hyperbilirubinemia (jaundice) and related conditions, such as Crigler-Najjar Syndrome. Any suitable type of garment is included within the scope of the present invention, with all garments constructed from a light-emitting fabric described below. The present invention enjoys many of its advantages due to its use of light-emitting diodes (LEDs) to deliver light directly to the neonate's skin. The LEDs are very small, very durable, and long-lasting. As a result, the garments are portable, lightweight, comfortable, easy to use, and relatively inexpensive. LEDs deliver relatively high light intensity for their physical size and weight with a relatively low power consumption (e.g., 70 mW), and therefore have high efficiency (optical output power/ electrical input power). They produce no harmful UV radiation and negligible heat (infrared).

In particular, the present invention uses surface-mounted LEDs, also known as chip-type LEDs, and not the more common lens-type or lamp-type LEDs. Lens LEDs contain a relatively large (e.g. 9 mm length and 3 or 5 mm diameter) bulbous lens used to focus the light at a particular angle, with two electrical leads extending from the bottom of the diode. They are thus relatively bulky and difficult to mount on a flexible surface. In contrast, surface-mounted LEDs are very small (e.g. 3 mm×2 mm×1 nm) and are mounted with their largest face contacting the surface and the leads extending sideways, so that they can easily be connected in series. Surface-mounted LEDs are therefore very well suited for incorporating into the garments of the present invention.

Figure 1A:
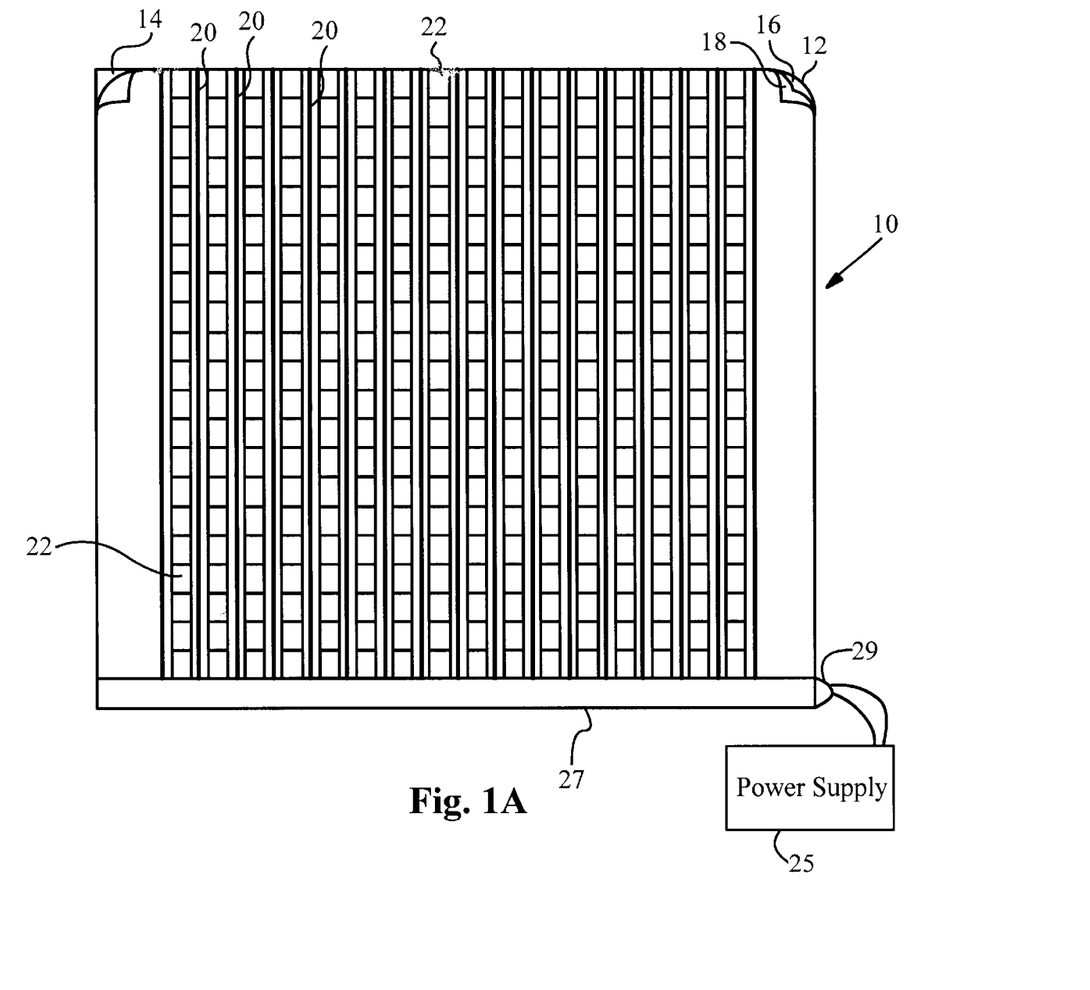
FIG. 1A is a top plan view of a preferred embodiment of a phototherapy garment of the present invention.
Figure 1B:
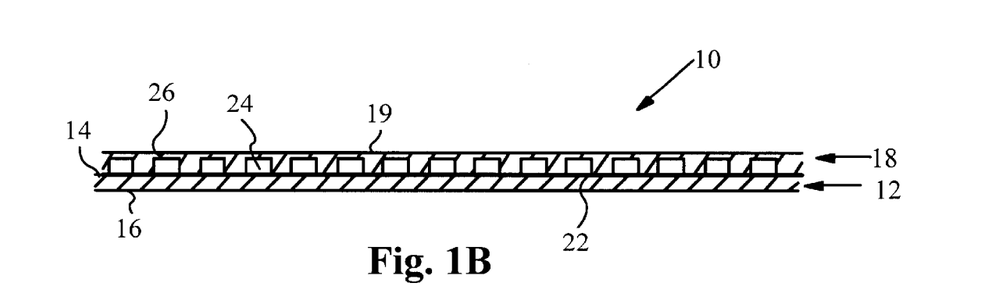
FIG. 1B is a cross-sectional view of the phototherapy garment of FIG. 1A.

A preferred embodiment of a phototherapy garment 10 is shown in FIGS. 1A and 1B. Phototherapy garment 10 is made of a flexible backing material 12 that has an inside surface 14 and an outside surface 16. Lining inside surface 14 of material 12 is a flexible liner 18, which has dimensions approximately equivalent to the dimensions of material 12. Liner 18 is made of a material that is substantially transparent to visible light, and particularly to the wavelength emitted by the light-emitting diodes described below. Liner 18 is sealed to material 12 only at particular locations, and not across its entire surface area. In FIG. 1A, liner 18 is fixed to material 12 at lines 20. For example, it may be crimped (heat-sealed), stitched, or molded to material 12. Sealing liner 18 to material 12 defines pockets between the two. These pockets are then used to secure a number of strips 22, which contain light-emitting diodes, to garment 10. If garment 10 is intended to encircle a neonate completely, it has suitable dimensions such as 20 inches by 16 inches. Of course, the dimensions of garment 10 may vary as desired or with the size of the neonate.

Preferably, material 12 and liner 18 are made of the same material and formed together. For example, they may be made of vinyl, silicone, or urethane. Because garment 10 directly contacts the jaundiced neonate, it is highly desirable that garment 10 can be cleaned and sterilized. The material should therefore be impervious to the solution, solvent, or gas used for cleaning or sterilization. In addition, the seal between material 12 and liner 18 should be impenetrable to any potential cleaning agent so that it does not contact the LEDs or electrical circuitry sealed inside. Alternatively, material 12 and liner 18 may be coated with an anti-bacterial coating, such as Medigard, manufactured by the Hydrogiene Corporation of San Diego, Calif. Medigard is formulated to kill a wide variety of bacteria, is resistant to cleaning and sterilization processes, and has a reputed four-year killing period. It can be coated in such a way as to be impossible to detach or destroy when applied to materials. Alternatively, garment 10 may be disposable, thereby alleviating the need for cleaning and sterilizing the garment.

Garment 10 contains strips 22 of flexible printed circuit sheets positioned between material 12 and liner 18. For example, strips 22 may be of mylar or other non-conductive material. Strips 22 contain printed circuits, such as copper traces, and surface-mounted light-emitting diodes 24. Producing printed circuit sheets and appropriate materials to use are known in the art. Strips 22 are secured to garment 10 by their placement in the pockets defined by backing material 12 and liner 18. Strips 22 are preferably sealed inside the pockets to allow a thorough cleaning of garment 10, such that cleaning material does not contacting strips 22. The light-emitting diodes 24 have light-emitting surfaces 26, and strips 22 are located in the pockets with these surfaces 26 facing liner 18, in which case the light-emitting diodes are said to be facing liner 18. While FIG. 1A shows sixteen strips 22, it is to be understood that any number of strips 22 may be used. In addition, they need not be strips, but may be any shape of printed circuit material. For example, a single sheet of printed circuit material may extend across the entire surface area of material 12. Preferably, as shown in FIG. 1B, material 12 and liner 18 are molded around strips 22 to form a smooth surface 19. For example, a urethane liquid may be cast around strips 22 and then cured until hardened. Liner 12 may also contain dispersants, i.e., particles that help disperse light generated by LEDs 24 to make it more uniform.

Figure 1C:
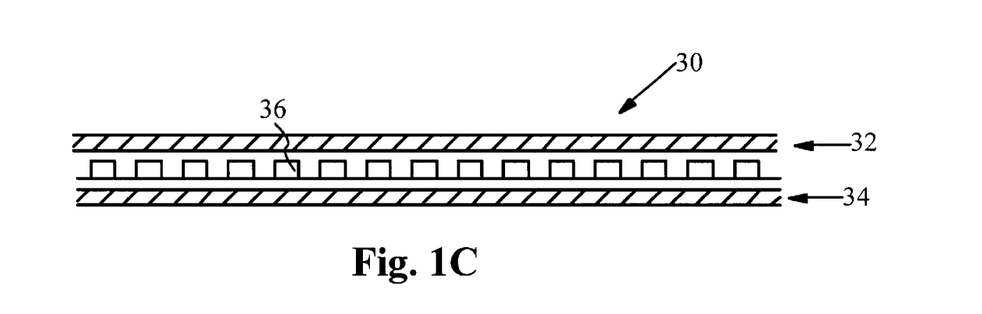
FIG. 1C is a cross-sectional view of an alternative embodiment of the garment of FIG. 1A.

FIG. 1C shows an alternative embodiment of a garment 30, in which the LEDs are positioned between a liner 32 and a backing material 34. Unlike in garment 10, liner 32 of garment 30 is not molded around the individual LEDs. Liner 32 is approximately 1 mm thick, and does not conform closely to LEDs 36. Garment 30 still presents a relatively smooth surface to the neonate. In addition, a combination of the two embodiments represented by FIGS. 1B and 1C can be made. That is, each strip of printed circuit sheet can be surrounded by the cast silicon or urethane, and then this strip inserted into a pocket in a vinyl material. In this embodiment, individual strips may be replaced if necessary.

Figure 2:
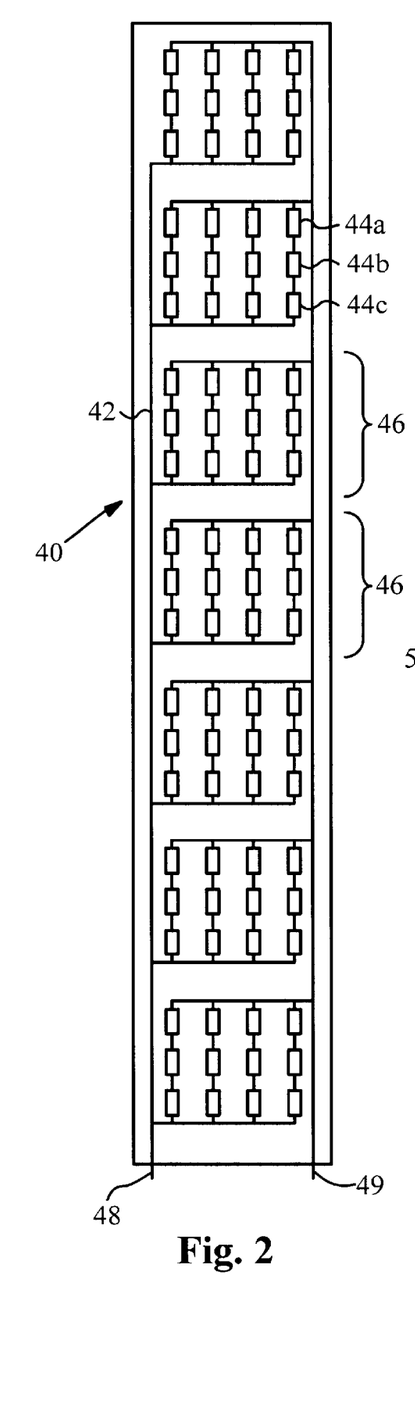
FIG. 2 illustrates a portion of a single printed circuit sheet containing light-emitting diodes, used in the garment of FIG. 1.

Each strip 22 of garment 10 is further divided into individual cells 46, shown in more detail in FIG. 2. For ease of illustration, FIG. 2 shows only seven individual cells 46. FIG. 2 illustrates a strip of flexible printed circuit sheet 40 containing a printed circuit 42 and an array of surface-mounted light-emitting diodes (LEDs) 44a, 44b, and 44c. LEDs 44a–c are preferably very small gallium-nitride-based LEDs that emit narrow-band blue light (450–490 nm), for example, broad-angle NSCB100 diodes from Nichia Chemical Industries, Ltd. (Japan). These LEDs are characterized by superior intensity and efficiency in the blue region of the spectrum, which is known to be most effective for converting bilirubin into products that are easily eliminated. LEDs 44a–c are also very compact, having dimensions of only 3 mm×2 mm×1 mm. Tightly-packed arrays of LEDs 44a–c are easily constructed, producing light that is uniform across the surface on which LEDs are fixed, rather than being localized to individual points. A density of 16 LEDs per square inch produces uniform light, but any suitable density may be used. Preferably, LEDs 44a–c are selected to have similar characteristics, i.e. similar spectral range and forward voltage, so that they produce light of substantially equal intensity. LEDs 44a–c contain two electrically conductive leads or pads that are connected to printed circuit sheet 40 by a solder joint as known in the art.

Each cell 46 preferably contains a number of LED strings connected in parallel. Within each string, the LEDs are connected in series. For example, in FIG. 2, each cell 46 contains four strings connected in parallel, with each string containing three LEDs connected in series, such as LEDs 44a, 44b, and 44c. All of the LEDs in a single strip are supplied current through two electrical leads 48 and 49. Of course, any arrangement of LED strings and any number of LEDs per string is within the scope of the present invention.

Referring again to FIG. 1A, a power supply 25 is electrically connected to a flexible electrical connector 27 at a connection 29. Flexible electrical connector 27 is connected in parallel to each of the two electrical leads exiting each printed circuit strip 22, such as leads 48 and 49 of FIG. 2, thereby connecting power supply 25 in parallel to each strip 22. With this configuration, current is supplied to the printed circuits and all LEDs. All individual cells, such as cells 46 of FIG. 2, are equivalent. Thus seven cells 46 are equivalent to 28 parallel strings of three LEDs in series. A thin electrical cable connects power supply 25 with flexible electrical connector 27. Power supply 25 is preferably a DC power supply or battery, and supplies a DC current. For safety, the power cord separating power supply 25 from garment 10 is at least three feet. Light intensity generated by LEDs 24 is determined by the current applied. Preferably, garment 10 provides an irradiance of at least 100 $\mu W/cm^2/nm$, which is more than double that produced by prior art fiber optic pads.

Connection 29 is a waterproof or moisture-proof electrical plug into which the electrical cord to power supply 25 is inserted to provide a waterproof seal. Connection 29 exits garment 10 through a sealed edge of flexible electrical connector 27; that is, even though connection 29 protrudes from garment 10, cleaning solutions cannot enter garment 10. Connection 29 is also able to withstand any desired cleaning treatment. To clean and sterilize garment 10, the electrical cord is removed from connection 29. After cleaning, when garment 10 is ready for reuse, the electrical cord is inserted back into connection 29.

Power supply 25 may be a standard portable power supply capable of generating a relatively low DC voltage, such as 12 or 24 V. Using a low voltage is desirable for reducing the risk of electrocution for the neonate under treatment. Appropriate circuitry is provided to control the current to the LEDs. Preferably, the current supplied to LEDs 24 is not constant, but is rather pulsed, with a duty cycle of approximately 10%. Each pulse has a maximum of approximately one second. Thus power supply 25 contains appropriate electronic circuitry to control the timing and activation of LEDs 24. Operating LEDs 24 at such a low duty cycle allows them to be overdriven, i.e., operated with a much higher applied current, for example, five times as high, than would be feasible with a constant current. Overdriving LEDs significantly increases their heat generation and decreases their lifetime; however, these drawbacks are compensated by the low duty cycle. The allowable ranges for duty cycle, forward current, and pulse width are determined by the LEDs themselves; such information is typically available from the LED manufacturer. While exposure of the neonate or nursery staff to the resultant pulsed light generated by LEDs 24 may be uncomfortable, such light is contained within garment 10, as discussed below, and therefore does not reach the eyes of the neonate or of nursery staff. Power supply 25 preferably has external controls that allow a person supervising the phototherapy to control the light intensity, frequency (i.e., pulse width), and duty cycle. It may instead have preprogrammed control circuitry that regulates the exposure time and other variables of the treatment.

The intermittent power may be supplied with any pulse width satisfying the LEDs' operating constraints. In vivo and in vitro studies are currently in progress to determine the optimum frequency and duty cycle for operating LEDs 24. Intermittent operation at higher power provides significantly more efficient bilirubin photoconversion than does constant operation at lower power. Bilirubin is produced primarily in the liver, transported in the blood stream, and enters the skin in significant amounts when the blood bilirubin concentration is quite high, leading to the characteristic yellowish skin tone; phototherapy is believed to affect bilirubin in the skin only. Bilirubin in the blood is constantly being exchanged with bilirubin and photoconversion products in the skin. This exchange takes a finite amount of time, typically longer than the reaction time for bilirubin conversion. When the light is off, the bilirubin concentration in the skin gradually builds up, and it is then converted when the light is on again. The LEDs are therefore used most efficiently when they are on a fraction of time, corresponding to the relative rates of the reaction time and the transport time into and out of the skin tissue.

Figure 3A:
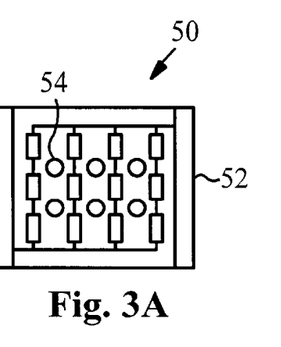
FIG. 3A shows a single cell of light-emitting diodes used in an alternative embodiment of the invention, in which portions of the garment are removed to facilitate cooling.
Figure 3B:
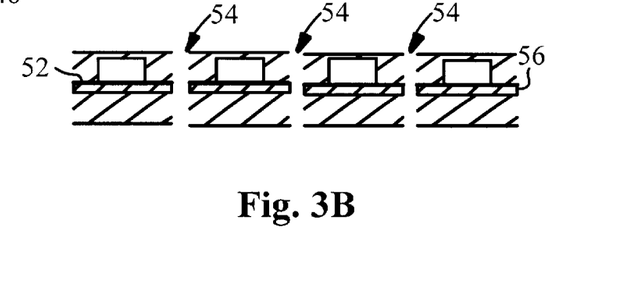
FIG. 3B is a cross-sectional view of the single cell shown in FIG. 4.

One of the distinct advantages of the present invention over prior art phototherapy devices is that it allows the neonate to be fully covered during phototherapy, and therefore much more comfortable and less susceptible to hypothermia. It also provides for cooling the neonate if the LEDs generate too much heat. Currently available LEDs produce high intensity light with low heat production, making heat dissipation manageable. An alternative embodiment of a single cell 50 is shown in FIGS. 3A and 3B. Flexible printed circuit sheet 52 contains removed portions 54, which are shown as circles, but may be any shape and size desired. Corresponding removed portions are located in the backing material and lining. Removed portions 54 allow transfer of water vapor from the neonate and improved heat removal from the skin of the neonate. Typically, removed portions 54 are circles with diameters of approximately 1–5 mm, and the garment appears perforated. Because the LEDs and circuitry must not contact the cleaning solution, the backing material and liner must be molded to the LED in order for the garment to have removed portions. When the garment is made, after the LEDs are sealed between the layers, the perforations or holes can be formed. In a combination of the embodiments of FIGS. 1B and 1C, the outer pockets may be a mesh or perforated structure; it is not necessary for the holes in the different layers to be aligned. If necessary, an external fan may be used to improve the heat removal by convection. Alternatively, a flexible, silicon-based heat sink material 56 may be positioned between the backing material and the printed circuit sheet for removing heat from the LEDs and minimizing the heat applied to the neonate's skin. As shown in FIG. 3B, heat sink material 56 may be used with a perforated garment, in which case heat sink material 56 should be perforated to correspond to removed portions of the garment.

It will be appreciated by a person of average skill in the art that many possible configurations of garment 10 are possible. For example, the configuration of FIG. 2 corresponds to a 12 V power supply. However, a 24 V power supply may be used, allowing each cell to have two strings of six LEDs each. In this configuration, half the amount of current is supplied, with the same power consumption and light generation, thereby decreasing the parasitic resistance of the circuitry. A 24 V power supply is still well within a safe voltage range. In addition, rather than a flexible printed circuit, a number of individual rigid circuit boards, each containing, for example, a single cell 46, may be connected by flexible traces to form a single strip. Note that such strips would allow the garment to be folded between individual strips, and also along the flexible traces between adjacent circuit boards. The flexible strips used in the embodiment described above are preferable, because they allow the entire strip to be bent in any desirable direction. When the entire strip must be bent, the configuration of FIG. 1B is preferable to the configuration of FIG. 1C. In the configuration of FIG. 1C, folding might cause the solder junctions connecting LEDs 24 to sheet 22 to break. Not only would this break the electrical connections and thus disable some of LEDs 24, it might also remove some LEDs 24 from sheet 22, which may be hazardous to the infant. In contrast, molding liner 18 around LEDs 24 helps prevent their removal from sheet 22. Of course, as new materials are developed, they may be incorporated into the present invention to help provide flexibility in any desired direction.

In an alternative embodiment of a phototherapy garment, a feedback system is included in power supply 25. A spectrophotometric sensor that measures the skin reflectivity, similar to a conventional jaundice meter, is in communication with the feedback system for providing an approximate measurement of the bilirubin level in the skin. Examples of jaundice meters are found in U.S. Pat. No. 5,353,790, issued to Jacques et al., and U.S. Pat. No. 4,029,085, issued to DeWitt et al. The method of Jaques et al. also measures reflectance of red, infrared, and yellow-orange light to determine the skin's maturity-dependent optical properties, melanin content, and the amount of blood, all of which are used to calculate the bilirubin content more accurately. The sensor may also be similar to a color measurement device described in U.S. Pat. No. 5,963,334, issued to Yamaguchi et al. During the dark periods, the jaundice meter periodically illuminates a small area of the skin with a pulse of white (i.e., broad spectrum) light; the blue light portion is absorbed by the bilirubin in the skin, leading to a decreased reflectance of blue light. The measured blue reflectance is converted into absorption and correlated with a bilirubin level. Alternatively, the sensor may measure reflectivity of the blue light generated by the LEDs. Reflectivity of two successive pulses is measured, and the increased reflectivity of the second pulse indicates the decrease in bilirubin levels. The feedback system may modify the intensity, frequency, or duty cycle of the light depending on the measured skin bilirubin level. Power supply 25 may also contain an indicator for displaying the bilirubin level or for indicating when the bilirubin concentration reaches a level at which phototherapy is no longer required or useful.

In a further alternative embodiment, power supply 25 includes a battery, replaceable or rechargeable, for supplying power to LEDs 24. The battery or batteries may be held in a pocket (not shown) attached to the outside surface of material 12, with appropriate circuitry for pulsing the LEDs contained in the pocket or on the inside surface of garment 10 and connected between the battery and the LEDs. Using a battery makes garment 10 fully portable, allowing it to be used when the neonate is transported to and from the hospital, for example.

Figure 4:
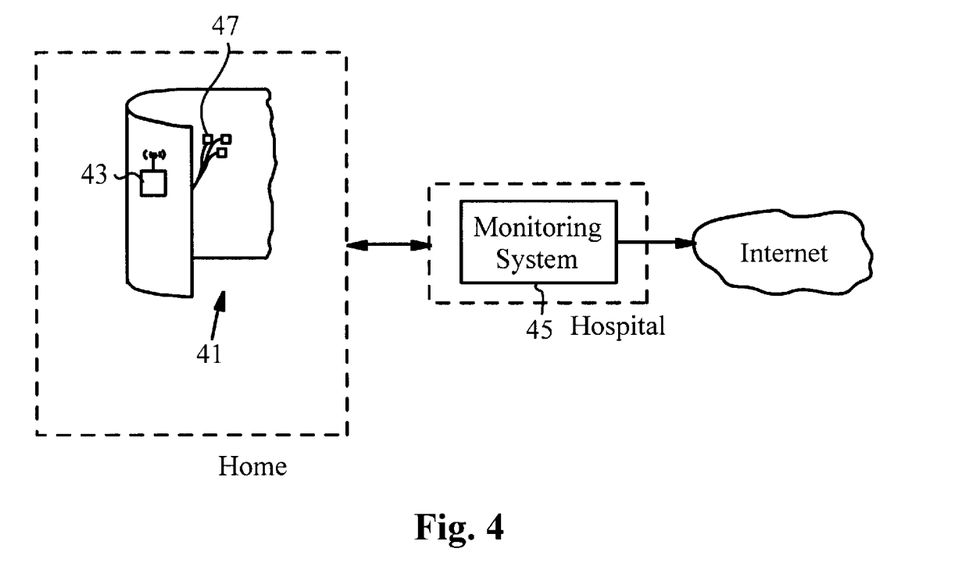
FIG. 4 is a schematic illustration of a phototherapy garment incorporating a communications device.

In a preferred embodiment, the garment is a "smart" phototherapy garment 41 as shown in FIG. 4. The smart phototherapy garment contains a two-way communications device 43, integrated with a portable power supply, that allows for communication between the device 43 and a monitoring system 45. Preferably, the communications device 43 is a wireless communications device such as a radio transmitter, for example, a mobile phone operating via base stations or satellite, or a two-way pager. Communication may also occur over a telephone line. The monitoring system 45 may itself be connected to the Internet, thus allowing for monitoring of the device and phototherapy treatment through a centralized transmission site accessed via a web site. The monitoring system 45 is preferably located at a doctor's office or hospital. Two-way communication allows for continual real-time monitoring of the newborn at home by the physician, thus providing for very safe at-home care. This embodiment of the invention is an example of biotelemetry, the remote detection and measurement of a human or animal function, activity, or condition, using techniques of radio-telemetry. Information on the history and current state of biotelemetry, particularly for laboratory animals, is found in K. Kramer et al., *Lab Animal*, 27(8): 40–46 (1998).

The communications device 43 sends two types of information to the monitoring system 45. The first type contains parameters of the phototherapy, such as the number of hours the garment has been on, when it was last turned on and off, and the current or light intensity used. It also, through the two-way communication link, allows the physician to turn the device on and off as necessary. While the home care giver is expected to operate the device, the monitoring system warns the physician if the device has not been turned on as expected or is malfunctioning. Garment 41 is therefore provided with appropriate circuitry to facilitate communication among the portable power supply, communications device 43, and LEDs.

The second type of information conveyed is that measured by skin sensors 47, which directly contact the infant's skin when the garment is worn. For example, skin sensors 47 may include a jaundice meter as described above. Correlation of the reflectance measurement with serum bilirubin level may be done within communications device 43, in which case it sends serum bilirubin levels to monitoring system 45, or by monitoring system 45, in which case communications device 43 sends reflectance measurements. Sensors 47 may be any sensors used to measure medical information non-invasively. For example, sensors 47 may determine skin temperature, oxygen saturation, glucose blood levels, or skin perspiration. Sensors 47 may also include a CCD (charge-coupled device) camera for imaging the skin. The various information sent may be used by the physician to modify the phototherapy parameters (e.g., treatment duration or light intensity). Alternatively, the monitoring system 45 may have an alarm system that notifies the physician when particular parameters are outside of acceptable ranges. For example, the physician may be paged or receive a telephone call with the relevant information. The physician may also be able to request exactly which parameters he or she is interested in obtaining.

A smart phototherapy garment 41 containing a two-way communications device and skin sensors, as provided by the present invention, provides dramatic advantages over existing phototherapy devices. Rather than being used in response to dangerously elevated bilirubin levels, the garment may be used prophylactically, to detect and manage increasing bilirubin levels. Bilirubin levels (and other important parameters) can be monitored continually for all newborns upon discharge from the hospital and in the critical few days immediately after discharge. If the serum bilirubin level reaches a threshold level (e.g. 10 mg/dl), then the garment either switches itself on or notifies a physician or caregiver to switch the garment on. Thus the present invention may actually eliminate the need for readmitting an infant to the hospital for phototherapy. It may also allow an infant to be discharged from the hospital sooner, because there is little risk that bilirubin levels will rise to dangerous levels. The garment also serves to keep a record of relevant medical parameters during the time that it is used.

Figure 5:
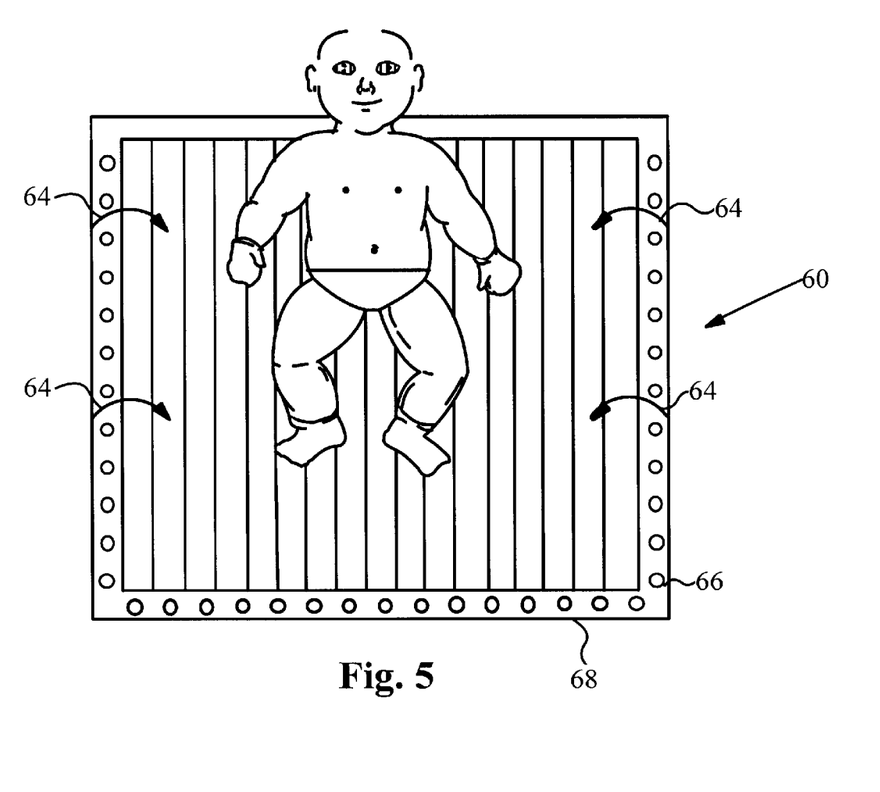
FIG. 5 illustrates placement of a neonate in a phototherapy garment of the invention.

FIG. 5 illustrates placement of a neonate inside a phototherapy garment 60 of the present invention. The neonate is placed with its longitudinal axis parallel to the printed circuit strips of the garment 60, and then garment 60 is folded around the circumference of the neonate, as shown by arrows 64. Note that light generated by garment 60 is incident on almost the entire surface area of the neonate, and is generated in close proximity to the skin, thereby providing both high irradiance and large surface area, two of the essential ingredients for efficient phototherapy. Fiber optic blankets in current use for phototherapy provide neither of these benefits, typically covering only a fraction of the neonate's skin and providing significantly lower light intensity. If the neonate is being fed intravenously and is covered with tubing, garment 60 may be left open, or may only cover as much of the neonate as possible. Garment 60 can also be opened and closed quickly and easily or removed from the neonate for frequent diaper changes or blood drawing.

To make garment 60 more comfortable for the neonate, it is preferably lined with a disposable gauze sheet that is substantially translucent or transparent to the emission wavelength of the LEDs. The gauze sheet may also help to keep garment 60 clean and facilitate perspiration removal by wicking liquid away from the skin and through the sheet. A newborn receiving phototherapy typically wears a diaper, even though a diaper decreases the surface area available for phototherapy. Newborns excrete approximately 120–180 ml of liquid per day, and thus it is not feasible for garment 60 itself to serve as a diaper. A preferable diaper to use with garment 60 is one that is transparent to the light emitted by the LEDs, but any small sized diaper may used. For example, a phototherapy diaper produced by BiliBottoms, Inc. of Hershey, Pa., is translucent to blue light, and therefore maximizes exposed skin surface area when used in combination with phototherapy garments of the present invention. Of course, garment 60 must be cleaned and sterilized at regular intervals as discussed above. Garment 60 may also be disposable, in which case it would be sterilized and packaged in a sterile container, and then disposed after a single use. Because the materials used to make garment 60 are relatively inexpensive, a disposable garment becomes more economically feasible as the price of LEDs continues to decrease.

Garment 60 is shown with snaps 66 positioned near edges 68. Snaps 66 or other suitable fasteners (e.g., zippers, Velcro) can be used to join edges 68 together and ensure that the neonate remains covered during treatment. Garment 60 is wrapped around the infant without covering its head; all of the generated light is therefore contained within the garment and does not interfere with the infant's vision. The contained light also does not disturb people in the vicinity of garment 60.

An optional cover layer (not shown) may be used and placed outside backing material 12. The cover layer may be any lightweight, flexible, and substantially opaque material, such as cotton or a synthetic fiber material. Preferably, it is "breathable," i.e., allows air and water vapor to flow through to aid in cooling. If desired, the cover layer may be decorated with patterns common to baby blankets or clothing.

Figure 6:
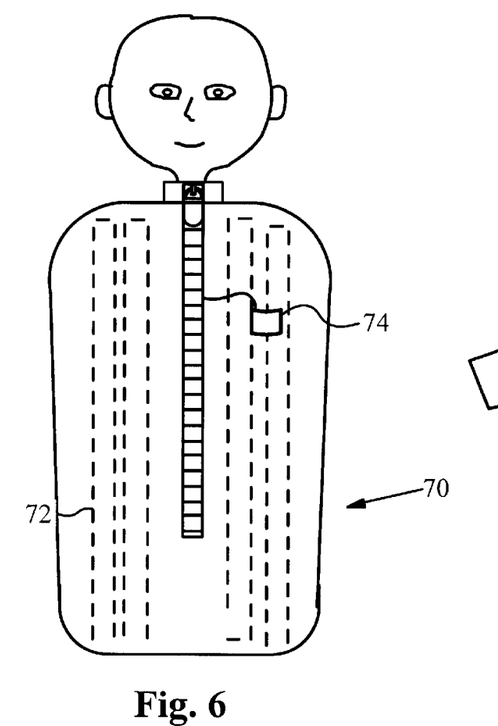
FIG. 6 shows a light-emitting sac of the present invention.

FIG. 6 shows an alternative embodiment of a phototherapy garment, a sac 70, a typical garment for a newborn, shown with an integral collar. While it might appear claustrophobic to an adult, newborns are quite content in such sacs, which contain zippers or other fasteners down the length of the garment for easy access to the newborn. Sac 70 is made out of a material similar to garment 10 of FIG. 1. Printed circuit strips 72 containing LEDs are located inside sac 70 to cover as much surface area of sac 70 as possible. Of course, other designs of the LED arrays than shown in FIG. 6 are possible, and LEDs may be placed in any desired portion of the garment. Sac 70 is particularly well suited for use during transport of an infant, and contains a pocket 74 for storing a battery used to power the LEDs. Sac 70 may also be used with a DC power supply for use in the home or in a hospital. Different portions or printed circuit strips of sac 70 may be controlled independently by using different power supplies, or may be powered by the same power supply. As with garment 60, light generated by sac 70 is contained substantially within sac 70, and does not interfere with the newborn's vision or require covering the newborn's eyes.

Figure 7A:
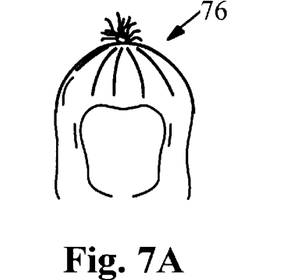
FIGS. 7A–C show alternative garments of the present invention.
Figure 7B:
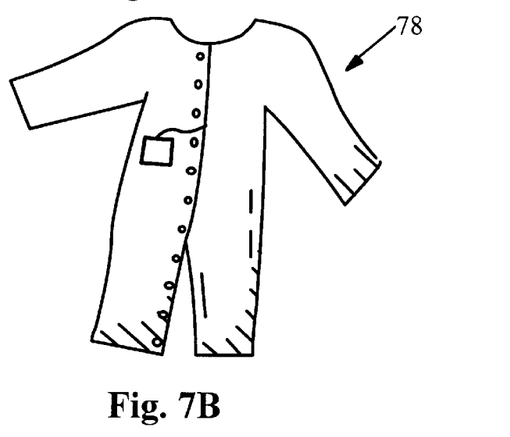
Figure 7C:
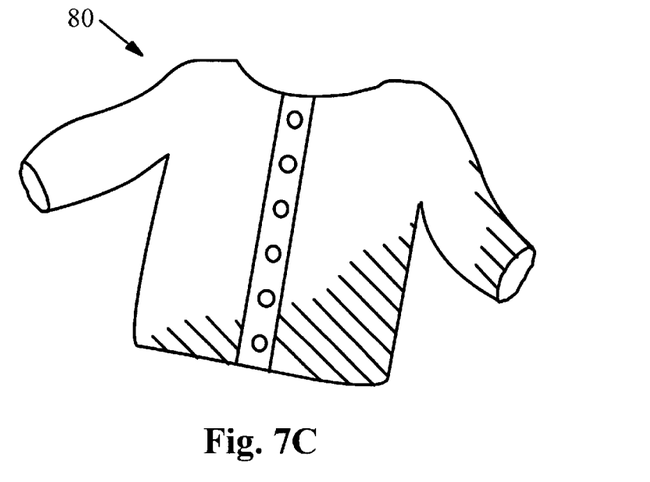

Phototherapy garment 10 can be considered to be a light-emitting fabric that can be used to make any number of other garments. Other examples of garments are shown in FIGS. 7A–C: a hat or mask 76, a romper 78, and a sweater or jacket 80. In the case of these more complicated garments, the flexible material forming the outside of the garment is referred to as a shell, which has a particular shape. Hat 76 is particularly useful as neonates have disproportionately large heads, with a high density of blood vessels, and the head therefore provides significant surface area over which phototherapy may be performed. The garments can also be used together. Because the garments do not interfere with the neonate's vision or sleep patterns, they can be worn as much as necessary, including overnight, thereby providing for rapid and efficient reduction of bilirubin levels. Each type of garment shown covers a particular skin region of the patient, for example, the torso, legs, or head. For each region, it is highly preferable that the light-emitting portions of the garment cover the entire circumference of the region, thereby illuminating the largest possible surface area of the region.

It is expected that sac 70, hat 76, romper 78, and jacket 80 will be made in a variety of sizes to fit differently sized infants. For example, premature infants may be significantly smaller than large-sized infants. Obviously, large infants will not fit into garments created for premature infants, and oversized garments are not safe for small infants. Furthermore, different types of garments may be better suited for only smaller or only larger infants. Very small newborns are more suited to garment 10 or sac 70, while larger infants are more suited to rompers, jackets, and other more complicated garments.

Treatment time using phototherapy garments of the present invention varies widely depending upon the conditions of the particular neonate, particularly the serum bilirubin level. However, it is expected that treatment times are significantly less than with existing treatments, which provide much lower irradiance and less surface exposure. Studies of the use of surface-mounted LEDs for phototherapy, carried out by the inventors of the present invention, are detailed in H. J. Vreman, R. J. Wong, D. K. Stevenson, R. K. Route, S. D. Reader, M. M. Fejer, R. Gale, and D. S. Seidman, "Light-Emitting Diodes: A Novel Light Source for Phototherapy," *Pediatr. Res.* 44: 804–809 (1998); and D. S. Seidman, J. M. Moise, Z. Ergaz, M. Stark, A. Laor, H. J. Vreman, D.K. Stevenson, and R. Gale, "A new blue light emitting phototherapy device compared to conventional phototherapy: a prospective randomized controlled application in term newborns," *Pediatrics*, in press (2000). In particular, these studies show the efficacy and safety of using blue LEDs as a light source for phototherapy.

The present invention can also be used to treat Crigler-Najjar syndrome, a genetic disorder in which the liver lacks an enzyme necessary to convert bilirubin into products that are easily excreted. Crigler-Najjar sufferers require nightly phototherapy to maintain bilirubin concentrations below a toxic level and typically live only until about age 30. For this application, a garment 10 is wrapped entirely around the patient's torso, and may be worn during regular daytime activity (e.g., school), which is usually limited by the disease. At night, the patient sleeps completely surrounded by a light-emitting garment that wraps around the entire body and extends from head to toe. Because the light is contained, it does not disturb the sleep patterns of the patient.

It will be clear to one skilled in the art that the above embodiment may be altered in many ways without departing from the scope of the invention. For example, LEDs may be arranged in other configurations than those shown here. LEDs emitting wavelengths of light other than blue wavelengths may used, and multiple different wavelengths may be used on the same garment. Phototherapy has been shown to cause a decrease in the endogenous levels of riboflavin, a natural photosensitizer. When irradiated by broad wavelength white or blue light, riboflavin produces singlet oxygen that may react with bilirubin and other organic compounds, causing photodamage and decreased riboflavin levels in developing neonates. Narrow wavelength blue to green LED light is less likely to be absorbed by endogenous photosensitizers and appears to produce fewer side effects, and thus LEDs with higher wavelengths (blue to green) may be included in the garments of the present invention. In addition, rather than use individual surface-mounted LEDs, a commercially available block of multiple diodes may be used. For example, a single cell of LEDs, or single rigid circuit board, can be replaced by a block of diodes. Liquid crystalline display (LCD) sheets may also be used in the garments, allowing for very accurate wavelength control. Accordingly, the scope of the invention should be determined by the following claims and their legal equivalents.

What is claimed is:

1. A phototherapy garment comprising:
   a) a flexible shell having an inside surface and an outside surface;
   b) a liner sealed to said inside surface of said flexible shell and defining a pocket between said shell and said liner;
   c) a flexible printed circuit sheet having a printed circuit and a plurality of surface-mounted light-emitting diodes electrically connected to said printed circuit, said printed circuit sheet being secured inside said pocket with said light-emitting diodes facing said liner, wherein said liner is substantially transparent to an emission wave length of said light-emitting diodes; and
   d) a power supply in electrical communication with said printed circuit, wherein said power supply intermittently provides power to said light-emitting diodes at a predetermined frequency and with a predetermined duty cycle.

2. The garment of claim 1 wherein said garment is selected from the group consisting of a hat, a sweater, a jacket, a romper, and a sac.

3. The garment of claim 1 wherein said duty cycle is less than 50%.

4. The garment of claim 1 wherein said duty cycle is approximately 10%.

5. A phototherapy garment comprising:
   a) a flexible backing material having an inside surface, an outside surface, and an edge;
   b) a liner sealed to said inside surface of said backing material and defining a pocket between said backing material and said liner;
   c) a printed circuit sheet having a printed circuit and a plurality of surface-mounted light-emitting diodes electrically connected to said printed circuit, said printed circuit sheet being secured inside said pocket with said light-emitting diodes facing said liner, wherein said liner is substantially transparent to an emission wavelength of said light-emitting diodes; and
   d) a power supply in electrical communication with said printed circuit, wherein said power supply intermittently provides power to said light-emitting diodes at a predetermined frequency and with a predetermined duty cycle.

6. The garment of claim 5 wherein said printed circuit sheet is a flexible printed circuit sheet.

7. The garment of claim 5 wherein said power supply comprises a portable power supply.

8. The garment of claim 5 wherein said power supply comprises means for supplying power intermittently to said light-emitting diodes.

9. The garment of claim 5 wherein said power supply comprises means for overdriving said light-emitting diodes.

10. The garment of claim 5 wherein said flexible printed circuit sheet covers a majority of said inside surface of said backing material.

11. The garment of claim 5 wherein two adjacent portions of said edge of said backing material are joined together to define an interior space surrounded by said liner, and wherein a neonate is positioned in said interior space.

12. The garment of claim 5 wherein said backing material, said liner, and said flexible printed circuit sheet have removed portions to allow heat removal through said removed portions.

13. The garment of claim 5 wherein said duty cycle is less than 50%.

14. The garment of claim 5 wherein said duty cycle is approximately 10%.

15. The garment of claim 5 further comprising a communications device in electrical communication with said light-emitting diodes.

16. The garment of claim 15 wherein said communications device is a two-way communications device.

17. The garment of claim 15 wherein said communications device is a wireless communications device.

18. The garment of claim 5 further comprising a skin sensor secured to said liner.

19. The garment of claim 18 wherein said skin sensor detects skin reflectance.

20. The garment of claim 18 wherein said skin sensor detects a property chosen from the group consisting of skin temperature, oxygen saturation, glucose blood level, and perspiration.

21. The garment of claim 5 wherein said light-emitting diodes are arranged in a two-dimensional array.

22. The garment of claim 21 wherein said array is densely packed, whereby said light-emitting diodes generate substantially uniform light.

23. The garment of claim 22 wherein said array has a density of approximately 16 light-emitting diodes per square inch.

24. The garment of claim 5 wherein said garment has an irradiance of greater than 30 $\mu W/cm^2/nm$.

25. The garment of claim 24 wherein said garment has an irradiance of greater than 100 $\mu W/cm^2/nm$.

26. The garment of claim 5 wherein said light-emitting diodes emit light of a wavelength suitable for treating hyperbilirubinemia in neonates.

27. The garment of claim 26 wherein said wavelength is between 420 and 500 nm.

28. The garment of claim 27 wherein said wavelength is between 440 and 470 nm.

29. A method of treating a neonate for hyperbilirubinemia comprising the steps of:
   a) providing a garment having a plurality of surface-mounted light-emitting diodes that emit light at a wavelength suitable for treating hyperbilirubinemia;
   b) covering a skin region of said neonate with said garment such that said light-emitting diodes face said skin region;
   c) intermittently providing sufficient power at a predetermined frequency and with a predetermined duty cycle to said light-emitting diodes to activate said light-emitting diodes.

30. The method of claim 29 wherein said garment is selected from the group consisting of a hat, a sweater, a jacket, a romper, and a sac.

31. The method of claim 29 further comprising the steps of measuring a serum bilirubin concentration of said neonate, and using said serum bilirubin concentration to control said activation of said light-emitting diodes.

32. The method of claim 29 further comprising controlling said activation of said light-emitting diodes from a remote location.

33. The method of claim 29 wherein said skin region has a circumference and said garment covers a majority of said circumference.

34. The method of claim 29 where in said duty cycle is less than 50%.

35. The method of claim 29 wherein said duty cycle is approximately 10%.

36. A method of treating a patient for Crigler-Najjar syndrome comprising the steps of:
   a) providing a garment having a plurality of surface-mounted light-emitting diodes that emit light at a wavelength suitable for bilirubin conversion;

b) covering a skin region of said patient with said garment such that said light-emitting diodes are facing said skin region; and c) intermittently providing sufficient power at a predetermined frequency and with a predetermined duty cycle to said light-emitting diodes to activate said light-emitting diodes.

37. The garment of claim 36 wherein said duty cycle is less than 50%.

38. The garment of claim 36 wherein said duty cycle is approximately 10%.

* * * * *